__United States Patent__ [19]

Mihara et al.

[11] 4,337,063

[45] Jun. 29, 1982

[54] COMPETITIVE IMMUNOASSAY USING SPECTRAL SENSITIZER LABEL

[75] Inventors: Yuji Mihara; Nobuhito Masuda, both of Minami-ashigara; Nobuo Hiratsuka; Takushi, both of Miyazako, Tokyo; Tadashi Ikeda, Minami-ashigara, all of Japan

[73] Assignee: Fuji Photo Film Co., Ltd., Kanagawa, Japan

[21] Appl. No.: 126,920

[22] Filed: Mar. 3, 1980

[30] Foreign Application Priority Data

Mar. 1, 1979 [JP] Japan .................................. 54-23964

[51] Int. Cl.$^3$ ...................... G01N 33/54; G01N 33/58
[52] U.S. Cl. .................................... 23/230 B; 23/915; 424/12
[58] Field of Search ......................... 23/230 B; 424/12

[56] References Cited

U.S. PATENT DOCUMENTS 3,791,932  2/1974  Shuurs ........................... 23/230 B X
4,205,952  6/1980  Cais .................................... 23/230 B

*Primary Examiner*—Sidney Marantz
*Attorney, Agent, or Firm*—Sughrue, Mion, Zinn, Macpeak & Seas

[57] ABSTRACT

Method for immunological analysis of a trace component(s) by labelling an antigen or antibody with a marker comprising causing an immune reaction using an antigen or antibody labelled with a spectral sensitizer as a marker, separating the labelled antigen or antibody from the resulting antigen-antibody reaction product, then bringing either the labelled antigen or antibody and the labelled antigen-antibody reaction product into contact with a silver halide, exposing the resulting system to light having a wavelength which the spectral sensitizer absorbs, developing the thus exposed silver halide and then measuring the resulting density.

Trace components can thus be photochemically detected and the amount present quantitatively determined. The method provides high reproducibility and high sensitivity comparable to radioimmunoassay but without any risk of radiation exposure.

4 Claims, 1 Drawing Figure

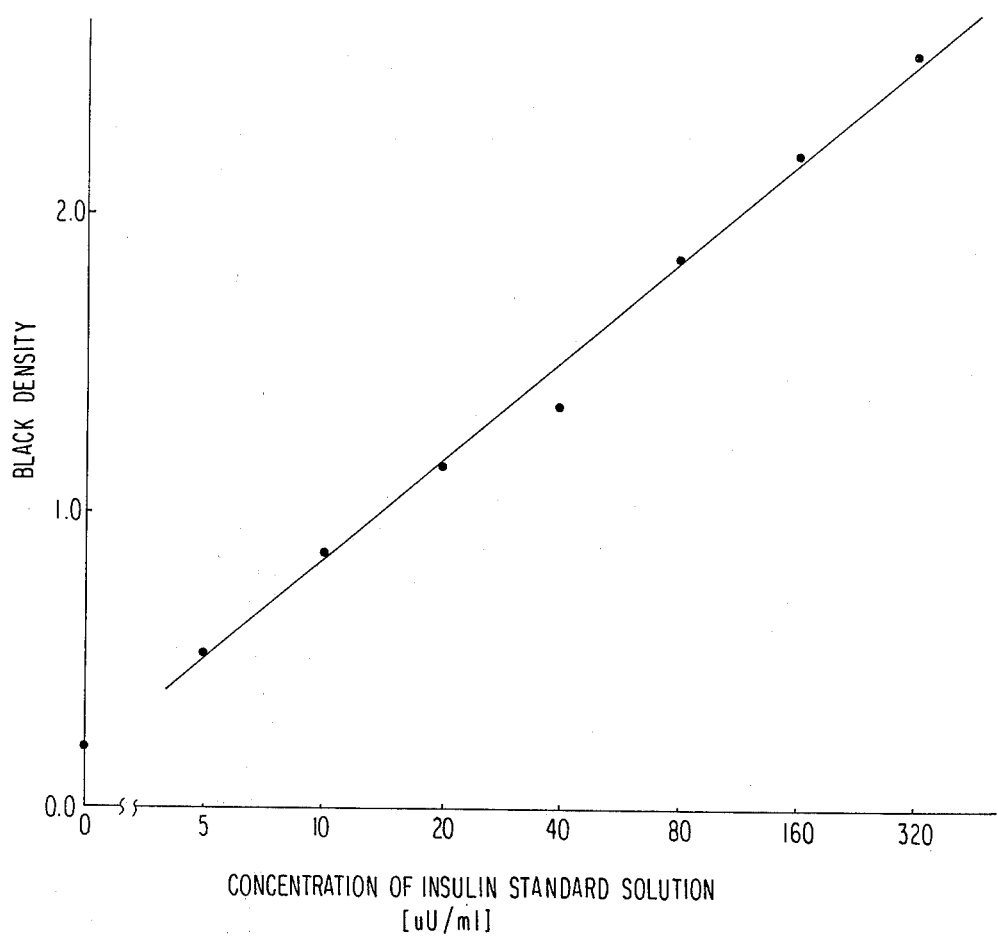

COMPETITIVE IMMUNOASSAY USING SPECTRAL SENSITIZER LABEL

BACKGROUND OF THE INVENTION

1. Field of the Invention

This invention relates to a method for immunologically analyzing a trace component(s), more particularly, to a method for photochemically analyzing a trace component(s) utilizing an immune reaction.

2. Description of the Prior Art

Radioimmunoassay (hereafter merely "RIA") is a method for the assay of a trace component(s) utilizing a specific antigen-antibody reaction. The basic principles of RIA are as follows. The reaction of a substance labelled or marked (hereafter the terms "label" and "mark" are used interchangably) with a radioactive isotope (RI) in a given amount and a substance having a specific binding affinity thereto in a given amount results in a coupled product of both of these components, while a part of the labelled substance remains in an unbound or unreacted free state. The reaction proceeds based on the laws of mass action in general, and, therefore, when an unlabelled substance is added to the reaction system, binding with a limited amount of binding protein is decreased and a certain relationship (calibration curve) is established therebetween. As a result, an amount of an unknown substance can be determined from the calibration curve if the bound substance and the labelled substance in the free state are separated and either one or both are measured with respect to RI amount.

Due to the high sensitivity and the simplicity of RIA, RIA is particularly applicable to the measurement and inspection of trace amounts of proteins in blood and hormones. Details thereon are given in, e.g., Kumahara and Shizume *NEW RADIOIMMUNOASSAY*, pages 3 to 10, 1977, published by Asakura Publishing Co., Ltd., Tokyo, *KISO SEIKAGAKU JIKKENHO* (Basic Biochemical Experiment) (6) and *SEIKAGAKUTEKI SOKUTEI* (Biochemical Assay), 1967, published by Maruzen Co., Ltd. Tokyo.

However, RIA is subject to several disadvantages due to the use of RI markers ($^{125}I$, $^{131}I$, etc.) as good markers are markers having highly specific radioactivity which maintain immune activity and are radioactively of high purity. For these reasons, RIA involves the danger of radiation exposure and it is necessary to manage expensive and unstable markers which cannot be used for extended periods of time. In addition, special installations, equipment and personnel qualified to deal with radiation are required. Finally, after RIA, disposal of radioactive waste material and the ensuing pollution problems are encountered.

SUMMARY OF THE INVENTION

Therefore, one object of this invention is to provide a method for determining the amount of a trace component(s) without any radiation danger and adequately high sensitivity.

As a result of investigating the quantitative immunological analysis of a trace component(s) present in solution, the inventors have found that the aforesaid object can effectively be achieved utilizing photochemistry.

The method in accordance with this invention relates to the immunological detection and quantitative analysis of a trace component(s) present in solution and comprises labelling an antigen or antibody with a spectral sensitizer for photographic use, i.e., an organic dye having an absorption region longer than the intrinsic absorption wavelength region of silver halide, preferably longer than 500 nm, bringing the organic dye combined with the antigen or antibody into contact with silver halide, exposing, developing and then measuring the density of the resulting developed silver amount or dye amount.

BRIEF DESCRIPTION OF THE DRAWING

The FIGURE shows a calibration curve, obtained in Example 1, for use of quantitative analysis of insulin.

DESCRIPTION OF PREFERRED EMBODIMENTS

More specifically, a known amount of a labelled antigen or labelled antibody is reacted with an antigen or antibody. After separating the reaction product and unreacted material, a quantitative assay of the marker of either one is performed using silver halide to prepare a calibration curve. Based on the calibration curve, an unknown amount of the antigen or antibody can be determined.

Spectral sensitizers for photographic use employed for labelling an antigen or antibody in this invention are well known as spectral sensitizers for photographic light sensitive materials. Cyanine dyes, merocyanine dyes, hemicyanine dyes, styryl dyes, etc. are representative thereof. Detailed disclosure of such spectral sensitizers is provided in *The Theory of the Photographic Process*, fourth edition, edited by T. H. James, 1977, published by MacMillian Co., *Cyanine Dyes and Related Compounds*, F. M. Hamer, 1964, Interscience Publishers, etc. Exemplary of specific dyes useful in this invention are merocyanine dyes as described in U.S. Pat. Nos. 2,493,748, 2,519,001 and 2,652,330; West German Pat. No. 1,177,841; French Pat. No. 1,412,702; British Pat. No. 489,335, etc.; cyanine dyes as described in U.S. Pat. Nos. 2,238,213, 2,503,776, 2,537,880, 3,196,017 and 3,397,060; West German Pat. Nos. 929,808, 1,028,718, 1,113,873, 1,163,671 and 1,177,482; French Pat. No. 1,359,683; British Pat. Nos. 840,223, 886,270, 886,271 and 904,332; Belgian Patent 654,816; Japanese Patent Publications No. 40-14112 and 40-23467, etc. These dyes can also be employed as a combination of two or more thereof. Supersensitization, including the use of the aforesaid dyes in combination with dyes as described in, e.g., Japanese Patent Publications Nos. 43-4932, 43-4936 and 43-22884 is also useful in this invention. Further, supersensitization as described in U.S. Pat. Nos. 2,947,630, 2,933,390, 2,937,089, 3,617,295 and 3,635,271 and French Pat. No. 1,500,218, etc., is also useful. Supersensitizers can be mixed together with the labelled antigen or antibody or can be previously incorporated into a silver halide emulsion.

Of these spectral sensitizers, sensitizers containing an amino, imino, mercapto, carboxy, amido or hydroxy group(s) therein are particularly preferred from an aspect of smooth labelling reaction.

As described above, spectral sensitizers having an absorption region longer than the intrinsic absorption wavelength region of silver halide are used in this invention. This is because it is necessary that silver halide latent images formed by intrinsic absorption of silver halide per se be differentiated from silver halide latent images formed by light absorption of the spectral sensitizers; the latter images are measured as the black density which would determine an unknown amount of a substance to be analyzed.

A method for labelling an antigen or antibody with a spectral sensitizing dye(s) (or a spectral sensitizer(s); these are interchangeably used in this invention) for photographic use involves chemical reaction, i.e., the spectral sensitizing dye(s) are reacted with an antigen or antibody through a covalent bond(s) to form a labelled reaction product. Reaction occurs between the spectral sensitizer(s) and functional groups contained in the antigen or antibody, e.g., an amino, imino, mercapto, carboxy, carbonamido, hydroxy, etc., group. The method of bond formation between both can be any of the following:

(1) Spectral sensitizers are directly reacted with the aforesaid functional groups;
(2) Spectral sensitizers and the aforesaid functional groups are reacted using an activating agent, and
(3) Spectral sensitizers and the aforesaid functional groups are reacted through a compound having a bifunctional group.

In these reactions, it is important that reaction conditions be chosen so as not to inhibit biological activities of the antigen or antibody to be marked. That is, a reaction temperature is generally between −20° and 60° C., preferably −8° C. and 40° C.; a reaction time is generally between 10 mins. and 16 hours; and a reaction pressure is between 1 and 20 atms., preferably atmospheric pressure. Where materials that tend to be volatilized are employed, it will be necessary that the reaction pressure be raised to, e.g., 20 atms. It is preferred that water or a pH buffering solution be employed as a solvent. Organic solvents such as DMF, methylene chloride, etc. are optionally used. These reaction conditions are generally common with those available for chemical modification of proteins and enzymes and are described in, e.g., PROTEIN, NUCLEIC ACID & ENZYME, 10, 1127 (1970), entitled "Chemical Modification of Enzyme and Protein—List of Publications for Respective Amino Acid Residues" by Soji Rokushika et al, and *SEIKAGAKU JIKKEN KOZA* (Lecture on Biochemical Experiment) I, 4th separate volume, pp. 10–203 (1977) edited by Nihon Kagakukai, published by Tokyo Kagaku Dojin, entitled "Chemical Modification of Protein".

Antigen or antibody materials containing reactive groups which provide bond formation as above described and the reactions thereof are described in detail in *SHINSENKAGAKU KOZA* (Lectures on New Biochemistry), 1, entitled "Chemistry of Protein", edited by Nihon Seikagakuka, published by Tokyo Kagaku Dojin, 1977; Izumiya, *PEPTIDE GOSEI* (Synthesis of Peptide), etc. One skilled in the art can easily perform such reactions for forming bonds from knowledge in the art and these publications.

Groups present in the spectral sensitizer that react with the aforesaid functional groups include those derived from:

alkyl chloroformates (e.g., diethyl chloroformate, isobutyl chloroformate, etc.), aldehydes (e.g., formaldehyde, glutaraldehyde, etc.), isocyanates (e.g., xylylene diisocyanate, tolylene diisocyanate, hexamethylene diisocyanate, etc.), thioisocyanates (e.g., xylylene dithioisocyanate, etc.), vinyl compounds (e.g., divinyl ketone, methylene bisacrylamide, divinylsulfone, etc.), active halides (e.g., cyanuric chloride, mucohalogenic acids, nitrophenyl chloride, phenol-2,4-toluenesulfonate, etc.), imidazoleamides (e.g., carbonyl diimidazole, sulfonyl diimidazole, triimidazolyl phosphate, etc.), pyridinium compounds (e.g., N-carbamoyl pyridinium, N-carbamoyloxypyridinium, etc.), sulfonic acid esters (e.g., alkane sulfonic acid esters, etc.), bismaleimides (e.g., N,N'-(1,3-phenylene)bismaleimide, etc.), diazonium compounds (e.g., bisdiazobentidine, etc.), epoxy compounds (e.g., bisoxysilane, etc.), acid anhydrides, carboxylic acids, ethyleneimines, and the like.

Typical examples of activating agents used in (2) above include alkyl chloroformates (e.g., diethyl chloroformate, isobutyl chloroformate, etc.) and sulfonic acid esters (e.g., alkane sulfonic acid esters, etc.).

These functional groups can inherently be present in the spectral sensitizers or can be introduced into the spectral sensitizers via chemical reaction(s) such as an addition reaction, a substitution reaction, a Schiff's base formation reaction, etc. directly or using compound having these functional groups.

Furthermore, the spectral sensitizer can be crosslinked and combined with an antigen or antibody using a compound (reagent having two or more functional groups (preferably 2 to 5)).

All of the above functional groups can be used singly or in combination.

Typical examples of these bifunctional groups for the antigen, antibody or marker include groups derived from compounds such as carbodiimides (e.g., 1-ethyl-3-(3-dimethylaminopropyl)carbodiimide, 1-cyclohexyl-3-(2-morphodinyl-4-ethyl)carbodiimide, N,N'-dicyclohexylcarbodiimide, etc.), isoxazoliums, psuedo bases, active esters (e.g., benzenesulfonic acid hydrosuccinimide ester, etc.).

The amount of spectral sensitizer(s) used for labelling an antigen or antibody varies depending upon kind of the antigen or antibody, but such is generally used in a molar ratio of 1 to 700 times that of the antigen or antibody, preferably 1 to 100 times, same basis.

Simple tests will be enough to confirm completion of labelling. Where it is confirmed utilizing absorption spectrum, following completion of the labelling reaction, an absorption spectrum of a separated and purified product is measured; if the resulting absorption spectrum is consistent with the intrinsic absorption spectrum which a spectral sensitizer possesses, it is confirmed that the labelling reaction is effected. A further method for confirming the labelling being effected is to analyze the presence or absence of the specific terminal groups, e.g., an amino or carboxy group(s). In case that the spectral sensitizer is introduced at the terminal amino group(s) of the spectral sensitizer, it is confirmed by the analysis of the N-terminal that completion of the labelling reaction has been effected if the corresponding amino acid(s) converted to an amino group(s)-on which labelling is to occur are not detectable. Detailed disclosure on such an N terminal analysis is described in, e.g., B. S. Hartley and V. Massey, *Biochim. Biophys. Acta*, 21, 58 (1956) (generally referred to as a Dansyl method in the art), *Archn. Biochem. Biophys.*, 22, 475 (1949) (a PTC (phenol isocyanate) method), F. Sanger, *Biochem. J.*, 39, 507 (1945) (a dinitrofluorobenzene method), etc. In a similar manner, the terminal carboxy group(s) are analyzed to check completion of the labelling reaction, details of which are given in, e.g., S. Akabori, K. Ohno and K. Narita, *Bull. Chem. Soc. Japan*, 25, 214 (1952) (generally referred to as a hydrazine decomposition method in the art), H. Matuo, U. Fujimoto and T. Tatuno, *Biochem. Biophys. Res. Comminication*, 22, 69 (1966) (a tritium marking method), etc. Further, details of these terminal determination methods are also given as a review in S. B. Needleman, *PROTEIN SEQUENCE DETERMINATION*, published by Springer Verlag (Berlin), 1975.

To separate the marked or labelled antigen-antibody reaction product or antigen-bound antibody (B) from the labelled free antigen or antibody (F) (hereafter this separation is often referred to as a B/F separation), various liquid chromatography techniques (e.g., gel filtration, ion exchange, partition chromatography, adsorption chromatography including affinity chromatography, microfilter filtration, dialysis, adsorption using cellulose, talc, dextran powder, etc., salting out (separation of precipitated and aggregated matters formed by adding a salt to a system, see, L. Wide and C. A. Gemzell, *Ciba Foundation Colloq. on Endocrinol.*, 14, 296 (1962)), precipitation (separation of crystallized specific protein formed due to difference of dielectric point, etc., which occurs by changing pH, see, G. M. Brodsky and P. H. Forsham, *J. Clin. Invest.*, 39, 1070 (1960)), centrifugation, crystallization, extraction, solid phase separation, etc., can be used. Detailed disclosure of these separation techniques is provided in Kazuo Shizume and Yuichi Kumahara, *NEW RADIOIMMUNOASSAY*, 1967, published by Asakura Publishing Co., Ltd., Tokyo.

Various methods can be used to bring the spectral sensitizer combined with the antigen, antibody or antigen-bound antibody into contact with silver halide, e.g., dropping onto a silver halide emulsion layer, dropping onto an emulsion solution containing silver halide and other methods of contacting with a silver halide emulsion layer or emulsion solution.

Of these methods, dropping the spectral sensitizer onto the surface of a silver halide emulsion is preferred. Silver halide having added thereto the spectral sensitizer by these methods or emulsions containing such silver halide are coated onto a support such as paper, cellulose acetate, polyester, etc., in a conventional manner.

Trace components which can be analyzed by this invention are typically trace components in the living body; drugs, in addition thereto, are amenable to analysis.

Examples of such trace components include peptide hormones (e.g., insulin, glucagon, parathyroid hormone, carcitonin, erythropoetin, secretin, cholecystokinin, gastrin, angiotensin II, vasopressin, oxytocin, melanin cell-stimulating hormone, adrenal cortex stimulating hormone, thyroid stimulating hormone, growth hormone, prolactin, corpus luteum stimulating hormone, follicle stimulating hormone); non-peptide hormones (e.g., steroid hormones such as glucocorticoid, aldosterone, adrenergic androgene, estrogene, progesterone, testosterone); other hormones such as thyroid hormones (eg., thyroxin, triiodothyronine), cortisol, estriol, adrenalin, noradrenalin, melatonin, acetylcholine; enzymes such as $C_1$-esterase, alkali phosphatase, pepsinogen, tripsin; kinase virus; specific antigens; tumor antigens (e.g., $\alpha$-fetroprotein); blood serum protein components (e.g., thyroxin-bound globulin, IgG, IgE); drugs (e.g., LSD, etc.); and others (e.g., rheumatism factor, myocin, etc.).

Specific examples of silver halides employed in this invention include silver chloride, silver chlorobromide, silver bromide, silver iodobromide, silver chloroiodobromide, silver chloroiodide, silver iodide, etc.

These silver halides can be emulsion dispersed or suspended in hydrophilic colloid binder solution or can be supported onto a support without any binder (e.g., a silver halide layer can be directly formed on a support by vacuum deposition, etc.).

Silver halide(s) contained in a photographic emulsion used in the present invention can be prepared in a conventional manner, e.g., by a single jet method, a double jet method, or a combination thereof. Useful preparation methods of silver halide emulsions are described in, e.g., Trivelli and Smith, *The Photographic Journal*, vol. 79, pp. 330–338 (1939), C. E. K. Mees, *The Theory of the Photographic Process*, 1966, published by MacMillian, Glafkides, *Photographic Chemistry*, vol. I, pp. 327–336, published by Fountain Press, etc.

The grain size of silver halide(s) in an emulsion(s) employed in this invention is conventional or smaller. It is thus generally preferred that the average grain diameter be 0.04 to 4microns (measurement of number average by the projected area method).

The silver halide emulsions employed in this invention are not chemically ripened but generally are chemically sensitized in a conventional manner, for example, by gold sensitization (as disclosed in U.S. Pat. Nos. 2,540,085, 2,597,876, 2,597,915 and 2,399,083, etc.), by sensitization with metal ions of Group VIII of the Periodic Table, by sulfur sensitization (as disclosed in U.S. Pat. Nos. 1,574,944, 2,278,947, 2,440,206, 2,410,689, 3,189,458 and 3,415,649, etc.), by reduction sensitization (as disclosed in U.S. Pat. Nos. 2,518,698, 2,419,974 and 2,983,610, etc.), or by a combination thereof.

Specific examples of chemical sensitizers include sulfur sensitizers such as allylthio carbamide, thiourea, sodium thiosulfate, cystine, etc.; noble metal sensitizers such as potassium chloroaurate, aurous thiosulfate, potassium chloropalladate, etc.; reduction sensitizers such as stannous chloride, phenylhydrazine, reductone, etc.; polyoxyethylene derivatives as described in British Pat. No. 981,470, Japanese Patent Publication No. 31-6475 and U.S. Pat. No. 2,716,062, etc.; polyoxypropylene derivatives, quaternary ammonium-containing derivatives, etc.

Silver halide emulsions which are employed in this invention can also contain suitable antifoggants and stabilizers. For example, specific antifoggants and stabilizers include thiazolium salts as described in U.S. Pat. Nos. 2,131,038 and 2,694,716, etc.; azaindenes as described in U.S. Pat. Nos. 2,886,437 and 2,444,605, etc.; urazoles as described in U.S. Pat. No. 3,287,135, etc.; sulfocatechols as described in U.S. Pat. No. 3,236,652, etc.; oximes as described in U.S. Pat. Nos. 2,403,927, 3,266,897 and 3,397,987, etc.; nitron; nitroindazoles; polyvalent metal salts as described in U.S. Pat. No. 2,839,405, etc.; thiuronium salts as described in U.S. Pat. No. 3,220,839, etc.; salts of palladium, platinum and gold as described in U.S. Pat. Nos. 2,566,263 and 2,597,915, etc.

Silver hallide emulsions which are used in this invention can also contain, if desired, one or more developing agents (e.g., hydroquinones, catechols, aminophenols, 3-pyrazolidones, ascorbic acid or derivatives thereof, reductones, phenylenediamines, etc.), or combinations of these developing agents. The developing agents can be incorporated into a light sensitive emulsion and/or other suitable layers (e.g., a hydrophilic binder layer) of a photographic element. The developing agents can be incorporated using a suitable solvent or in the form of a disperson as described in U.S. Pat. No. 2,592,368 or French Pat. No. 1,515,778.

Silver halide emulsions employed in this invention can contain coating aids such as saponin, alkyl aryl sulfonates as described in U.S. Pat. No. 2,600,831, etc., amphoteric compounds as described in U.S. Pat. No. 3,133,816, etc. and can further contain antistatic agents, plasticizers, fluorescent whitening agents, developing accelerating agents, air antifogging agents, color toning agents, etc.

As the silver halide emulsion(s) used in this invention, gelatin silver halide emulsions are generally employed but this is not mandatory. For example, instead of gelatin substances that do not adversely affect light sensitive silver halides such as albumin, agar, gum arabic, alginic acid, acylated gelatin (e.g., phthalated gelatin, malonated gelatin, etc.), hydrophilic polymers such as polyvinyl alcohol, polyvinylpyrrolidone, polyacrylamide, polystyrene sulfonic acid, cellulose compounds (e.g., hydroxethyl cellulose, carboxymethyl cellulose, dextrin, etc.), water-soluble starch, etc., can be used. Further, combinations thereof can be used.

Photographic emulsion layers of photographic light sensitive materials used in this invention can contain color image-forming couplers, that is, compounds capable of forming dyes by reaction with the oxidation product of an aromatic amine (normally a primary amine) developing agent (hereafter referred to as a coupler). It is preferred that the coupler be non-diffusible and comprise a hydrophobic group(s) called a ballast group(s) in the molecule thereof. The coupler(s) can be four-equivalent or two-equivalent to silver ions. In addition, the photographic emulsion layers can also contain colored couplers having a color correction effect or couplers releasing a development inhibitor upon development (DIR couplers). The couplers also can be couplers where the product of the coupling reaction is colorless.

As yellow color-forming couplers, known open chain ketomethylene type couplers can be used. Of these, benzoylacetanilide type and pivaloyl acetanilide type compounds are preferred. Specific examples of yellow-color-forming couplers are described in U.S. Pat. Nos. 2,875,057, 3,265,506, 3,408,194, 3,551,155, 3,582,322, 3,725,072, and 3,891,445; West German Pat. No. 1,547,868; West German Patent Applications (OLS) Nos. 2,219,917, 2,261,361 and 2,414,006; British Pat. No. 1,425,020; Japanese Patent Publication No. 51-10783; Japanese Patent Application Laid Open (OPI) Nos. 47-26133, 48-73147, 51-102636, 50-6341, 50-123342, 50-130442, 51-21827, 50-87650, 52-82424 and 52-115219, etc.

As magenta color-forming couplers, pyrazolone type compounds, indazolone type compounds, cyanoacetyl compounds, etc., are preferred. Of these, pyrazolone type compounds are particularly preferred. Specific examples of magenta color-forming couplers which can be employed are those described in U.S. Pat. Nos. 2,600,788, 2,983,608, 3,062,653, 3,127,269, 3,311,476, 3,419,391, 3,519,429, 3,558,319, 3,582,322, 3,615,506, 3,834,908, and 3,891,445; West German Patent 1,810,464; West German Patent Application (OLS) Nos. 2,408,665, 2,417,945, 2,418,959 and 2,424,467; Japanese Patent Publications 40-6031 and 51-45990; Japanese Patent Application Laid Open (OPI) Nos. 51-20826, 52-58922, 49-129538, 49-74027, 50-159336, 52-42121, 49-74028, 50-60233, 51-26541 and 53-55122, etc.

As cyan color-forming couplers, phenol type compounds, naphthol type compound, etc., are preferred. Specific examples include those described in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929; West German Patent Applications (OLS) 2,414,830 and 2,454,329; Japanese Patent Application Laid Open (OPI) Nos. 48-59838, 51-26034, 48-5055, 51-146828 and 52-69624 and 52-90932, etc.

As colored couplers, those described in, e.g., U.S. Pat. Nos. 3,476,560, 2,521,908 and 3,034,892; Japanese Patent Publications 44-2016, 38-22335, 42-11304 and 44-32461; Japanese Patent Application Laid Open (OPI) Nos. 51-26034 and 52-42121; and West German Patent Application (OLS) 2,418,959, etc. can be used.

As DIR couplers, those described in, e.g., U.S. Pat. Nos. 3,227,554, 3,617,291, 3,701,783, 3,790,384 and 3,632,345; West German Patent Applications (OLS) 2,414,006, 2,454,301, and 2,454,329; British Patent 953,454; and Japanese Patent Application Laid Open (OPI) Nos. 52-69624, 49-122335 and 52-69624, Japanese Patent Publication 51-16141, etc., can be employed.

Compounds releasing development inhibitors with development can also be present in addition to DIR couplers. For example, compounds as described in U.S. Pat. Nos. 3,297,445 and 3,379,529; West German Patent Application (OLS) 2,417,914; and japanese Patent Application Laid Open (OPI) Nos. 52-15271 and 53-9116, etc., can be employed.

The aforesaid couplers can be incorporated in the same layer or in two or more difficult layers. The same compound can also be present in two or more different layers.

These couplers are generally added to an emulsion layer in an amount of $2 \times 10^{-3}$ to $5 \times 10^{-1}$ mol per 1 mol of silver, preferably $1 \times 10^{-2}$ to $5 \times 10^{-1}$ mol, same basis.

To introduce the aforesaid couplers into a silver halide emulsion layer, conventional methods as described in U.S. Pat. No. 2,322,027 can be employed. For example, these couplers can be dissolved in an alkyl phthalate(s) (dibutyl phthalate, dioctyl phthalate, etc.), a phosphoric acid ester(s) (diphenyl phosphate, triphenyl phosphate, tricresyl phosphate, diocytl butyl phosphate), a citric acid ester(s) (e.g., tributyl acetylcitrate, etc.), a benzoic acid ester(s) (e.g., octyl benzoate, etc.), an alkylamide(s) (e.g., diethyl lauryl amide), a fatty acid ester(s), e.g., dibutoxyethyl succinate, dioctyl azelate), etc., or into an organic solvent(s) having a boiling point of about 30° to about 150° C., e.g., a lower alkyl acetate(s) such as ethyl acetate, butyl acetate, etc., or ethyl propionate, secondary butyl alcohol, methyl isobutyl ketone, beta-ethoxethyl acetate, methyl cellosolve acetate, etc., and the solution then dispersed to a hydrophilic colloid. The aforesaid high boiling point organic solvent(s) can also be used in combination with the aforesaid low boiling point organic solvent(s).

Where couplers contain an acid group(s) such as a carboxylic acid or sulfonic acid group, they are introduced into a hydrophilic colloid as an aqueous alkaline solution.

In addition to the above high boiling point organic solvents, other high boiling point organic solvents can also be employed, and specific examples thereof include those described in, e.g., U.S. Pat. Nos. 2,322,027, 2,533,514, and 2,835,579; Japanese Patent Publication No. 46-23233; U.S. Pat. No. 3,287,134; British Pat. No.

958,441; Japanese Patent Application Laid Open (OPI) No. 47-1031; British Pat. No. 1,222,753; U.S. Pat. No. 3,936,303, Japanese Patent Application Laid Open (OPI) Nos. 51-26037 and 50-82078; U.S. Pat. Nos. 2,353,262, 2,852,383, 3,554,755, 3,676,137, 3,676,142, 3,700,454, 3,748,141 and 3,837,863; West German Patent Application (OLS) 2,538,889, Japanese Patent Application Laid Open (OPI) Nos. 51-27921, 51-27922, 51-26035, 51-26036 and 50-62632, Japanese Patent Publication 49-29461, U.S. Pat. Nos. 3,936,303, 256,658; Japanese Patent Application Laid Open (OPI) No. 53-1521, etc.

Various light sources can be employed for exposing the silver halide(s) brought into contact with the organic dye combined with an antigen or antibody in the present invention. For exposure, the light has wavelengths that the organic dye absorbs; other light as having a wavelength in the absorption region intrinsic to silver halide is filtered out. A suitable exposure degree is generally from $10^1$ to $10^{10}$ cms. As light sources, for example, a tungsten lamp, a halogen lamp, a mercury lamp, a xenon lamp, etc., can be employed in combination with a suitable optical filter (e.g., a shart cut filter manufactured by Fuji Photo Film Co., Ltd.). In addition, a solid laser (e.g., a ruby laser, etc.), a semiconductor laser (e.g., a lead sulfide laser, etc.), a dye laser, a gas laser (e.g., a neon helium laser, an argon laser, etc.), etc., can be advantageously employed.

Development processing performed in this invention is conventional and details thereof are given in L. F. Mason, *PHOTOGRAPHIC PROCESSING CHEMISTRY*, The Focal Press (1966), T. H. James, *THE THEORY OF THE PHOTOGRAPHIC PROCESS*, 4th edition, pages 291–334 and pages 373–403 (1977), Macmillan Publishing Co., Inc. (1977). That is, where an emulsion(s) is coated onto a support, development can be carried out in accordance with methods conventionally used for photographic development. More specifically, methods of development processing conventional photographic films or printing paper, etc., can be employed. For example;

(1) color development→stop→bleach→wash→fix→wash→stabilization→dry, (2) color development→stop→bleach→fix→wash→stabilization→dry, (3) color development→stop-fix→bleach→fix→wash→stabilization→dry, or (4) color development→bleach→wash→fix→wash→stabilization→dry.

In processings (1) to (4), a pre-bath, a hardening batch, etc., may be employed before the color development and also a stabilization or a wash after bleach may be omitted.

(5) black and white development→stop→bleach→wash→fix→wash→stabilization→dry, (6) black and white development→stop→fix→wash→stabilization→dry, (7) black and white development→stop-fix→wash→stabilization→dry, (8) black and white development→wash→fix→wash→stabilization→dry.

On the other hand, processings for color reversal films are fundamentally composed of the following steps:

(9) black and white development→stop→wash→fogging→wash→color development→stop→wash→bleach→wash→fix→wash→stabilization→dry or

(10) black and white development→stop→wash→fogging→wash→color development→stop→wash→bleach→fix→wash→stabilization→dry.

Developing solutions having the compositions as indicated in the examples hereinafter are typically used in the above processings.

Typical examples of fixing solutions and bleaching solutions are shown below.

| Composition of Fixing Solution: | | |
|---|---|---|
| | Acidic-Non-Hardening Type | Acidic-Hardening Type |
| Water (ml.) | 500 | 600 |
| Sodium thiosulfate (g) | 240 | 240 |
| Sodium thiosulfite, anhydrous (g) | 10 | 15 |
| Sodium hydrogen sulfite (g) | 25 | — |
| Acetic acid(28%) (ml.) | — | 48 |
| Boric acid (g) | — | 7.5 |
| Potassium alum (g) | — | 15 |
| Water to make | 1 liter | 1 liter |

| Composition of Bleaching Solution: | | |
|---|---|---|
| Kind | Major Ingredient | Application |
| Simple bleaching solution | acidic bichromates | black-and-white reversal |
| Rehalogenation bleaching solution | ferricyanides-potassium bromide | color reversal |
| Blix solution | $Fe^{3+}$- EDTA-thiosulfates | color paper |
| Bleach-stabilization solution | ferricyanides-thiocyanates | stabilization, no coloration |

In addition, development and other photographic processing can also be carried out by extending onto, coating onto, immersing in or spraying onto a support having coated thereon an emulsion various photographic processing agents. Further, where an emulsion is in the liquid state, photographic processing can be performed by adding to and mixing with the liquid emulsion the desired photographic agents.

The thus exposed emulsion layer is then processed by conventional photographic processing, i.e., as processing solutions, known processing solutions can be employed.

The processing temperature is generally selected between 18° and 50° C., but can be lower than 18° C. or higher than 50° C. Depending upon the purpose, any development processing forming silver images (black-and-white photographic processing) and color photographic processing comprising development processing to form color images can be used.

Developing solutions used in the case of black-and-white photographic processing can contain known developing agents. As such developing agents, dihydroxybenzenes (e.g., hydroquinone), 3-pyrazolidones (e.g., 1-phenyl-3-pyrazolidone), aminophenols (e.g., N-methyl-p-aminophenol), 1-phenyl-3-pyrazolines, ascorbic acid, and heterocyclic compounds comprising a condensed 1,2,3,4-tetrahydroquinoline ring and an indolene ring as described in U.S. Pat. No. 4,067,872, etc., can be used singly or as a combination thereof.

The developing agent solutions can generally contain known preservatives, alkali agents, pH buffers, antifogging agents, and, if necessary, dissolution aids, color toning agents, development accelerators, surface active agents, defoaming agents, softening agents, hardening agents, viscosity-imparting agents, etc.

"Lith" type development processing can also be applied to the photographic emulsion of this invention. The term "lith" type development processing refers to development processing which comprises, for the purpose of photographic reproduction of line images or photographic reproduction of half tone images using dots, infectious development at a low concentration of sulfite ions generally using a dihydroxybenzene(s) as a developing agent, the details of which are given in *Photographic Processing Chemistry*, Mason, 163–165 (1966).

As a special aspect of development, a developing method which comprises treating a light sensitive material in which a developing agent is contained, e.g., in an emulsion layer, in an aqueous alkaline solution can be used. Of such developing agents, a hydrophobic type can be incorporated into an emulsion layer by latex dispersion, as disclosed in *Research Disclosure*, No. 169, RD-16928. Such development processing can also be used in combination with silver salt stabilization, e.g., with a thiocyanate(s).

As fixing solutions, those having compositions conventionally used in photographic processing can be employed, e.g., as fixing agents, organic sulfur compounds such as thiosulfates, thiocyanates and other organic sulfur compounds that are known as having a fixing effect can be employed. The fixing solution can also contain water soluble aluminum salts as a hardening agent.

To form dye images, again conventional methods are used. A nega-posi method (e.g., as described in *Journal of the Society of Motion Picture and Television Engineers*, vol. 61, 667–701 (1953)) can also be used; further, a color reversal method which comprises developing with a developer containing a black-and-white developing agent to form negative silver images, then performing at least one overall exposure or other suitable fogging treatment and subsequently color developing to obtain positive color images can also be used; also, a silver dye bleach method which comprises exposing a photographic emulsion layer containing a dye, developing to thereby form silver images, and then bleaching the dye using the silver images as a bleaching catalyst, etc., can be used.

In general, a color developer comprises an aqueous alkaline solution containing a color developing agent. As color developing agents, known primary aromatic amine developing agents, for example, phenylenediamines (e.g., 4-amino-N,N-diethylaniline, 3-methyl-4-amino-N,N-diethylaniline, 4-amino-N-ethyl-N-beta-hydroxyethylaniline, 3-methyl-4-amino-N-ethyl-N-beta-hydroxyethylaniline, 3-methyl-4-amino-N-ethyl-N-beta-methanesulfamidoethylaniline, 4-amino-3-methyl-N-ethyl-N-beta-methoxyethylaniline, etc.) can be used.

In addition, compounds as described in L.F.A. Mason, *Photographic Processing Chemistry*, 226–229, 1966, Focal Press; U.S. Pat. Nos. 2,193,015 and 2,592,364; and Japanese Patent Application Laid Open OPI No. 48-64933, etc., can be used.

The color developer can also contain a pH buffering agent such as a sulfite, carbonate, borate and phosphate of an alkali metal, a development inhibitor or an antifogging agent such as a bromide, iodide or an organic antifogging agent, etc. The color developer can also contain, if necessary, a hard water softener, a preservative such as hydroxylamine, an organic solvent such as benzyl alcohol or diethylene glycol; a development accelerator such as polyethylene glycol, a quaternary ammonium salt or an amine; a dye forming coupler, a competing coupler, a fogging agent such as sodium borohydride, an auxiliary developing agent such as 1-phenyl-3-pyrazolidone, a viscosity imparting agent, a polycarboxylic acid type chelating agent as described in U.S. Pat. No. 4,083,723, an antioxidant as described in German Patent Application (OLS) 2,622,950, etc. Of course, combinations of the above materials can also be used.

The photographic emulsion layers after color development are usually subjected to bleaching. Bleaching can be performed with fixing at the same time or separately therefrom. Representative examples of bleaching agents include polyvalent metal compounds of iron (III), cobalt (III), chromium (VI), copper (II), etc., peroxides, quinones, nitroso compounds, etc. For example, ferricyanides, bichromates, inorganic complexes of iron (III) or cobalt (III), aminopolycarboxylic acids such as ethylenediamine tetraacetic acid, nitrilotriacetic acid, 1,3-diamino-2-propanol tetraacetic acid, etc., complexes of organic acids such as citric acid, tartaric acid, maleic acid, etc.; persulfates, permanganates; nitrosophenol, etc., can be employed. Of these, potassium ferricyanide, ethylene diamine tetraacetic acid iron (III) sodium and ethylene diamine tetraacetic acid iron (III) ammonium are particularly useful both in an independent bleaching solution and in a mono bath bleaching-fixing solution.

The bleaching or blix solutions can also contain bleach accelerators as described in U.S. Pat. Nos. 3,042,520 and 3,241,966 and in Japanese Patent Publications 45-8506 and 45-8836, etc., thiol compounds as described in Japanese Patent Application Laid Open (OPI) No. 53-65732 and other various additives.

Processing solutions which used in this invention can be liquid compositions containing processing components necessary for the development of silver halide emulsions and the formation of diffusion transfer dye images in which the major portion of the solvent is water and wherein a hydrophilic solvent(s) such as methanol, methyl cellosolve, etc., can also optionally be present in addition to water.

The processing compositions should have a pH necessary for development of the emulsion layers and should contain alkali in an amount sufficient to neutralize acids (e.g., hydrogen halides such as hydrogen bromide, carboxylic acids such as acetic acid, etc.) released during various steps for developing and forming dye images. As the alkali, alkali metal or alkaline earth metal salts, e.g. lithium hydroxide, sodium hydroxide, potassium hydroxide, a calcium hydroxide dispersion, hydroxylated tetramethyl ammonium, sodium carbonate, trisodium phosphate, diethyl amine, etc., or other amines are illustrative. Preferably, the alkali is an alkali hydroxide and imparts a pH of at least about 12 at room temperature, more preferably a pH of at least 14.

More preferably, the processing compositions contain hydrophilic polymers such as high molecular weight polyvinyl alcohol, hydroxyethyl cellulose, sodium carboxymethyl cellulose and the like. These polymers impart a viscosity of at least 1 poise at room temperature, preferably several hundred (500 to 600) to 1000 poise to the processing compositions to thereby not only provide uniform development upon processing but also to permit easy transfer of aqueous solvent into the light sensitive element and an image receiving element during processing, where, when the processing compositions are condensed, a non-fluid layer can be formed to assist that a film unit be firmly united after processing. Such a hydrophilic polymer layer prevents, after the formation of a diffusion transfer color image is substantially complete, further transfer of the colored component into the image receiving layer to thereby help prevent image changes.

In some cases, it is advantageous that the processing compositions also contain light absorbing substances such as $TiO_2$, carbon black, pH indicators, or desensitizers as described in U.S. Pat. No. 3,579,333, in order to prevent a silver halide(s) from being fogged by external light. In addition, the processing compositions can also contain development inhibitors such as benzotriazole. The aforesaid processing compositions can be used by encasing the same in a rupturable container as described in U.S. Pat. Nos. 2,543,181, 2,643,886, 2,653,732, 2,732,051, 3,056,491, 3,056,492 and 3,152,515, etc.

According to the method of this invention, detection sensitivity of trace components is high and excellent results of precise accuracy and reproducibility are obtained.

The markers used in the method of this invention do not involve the hazards of radiation as does radioimmunoassay since the markers, i.e., spectral sensitizers, are not radioactive; measurement and inspection can easily be performed by a person not necessarily qualified to deal with radioactives and, in addition, storage of the markers for a long period of time due to the excellent stability thereof is possible. Further, densitometers as are conventionally used in the photographic arts can be used as measurement equipment so that measurement can be made simply and at low cost.

In the following examples, all percents are by weight, and reactions were performed at ambient temperature under atmospheric pressure, unless otherwise indicated.

EXAMPLE 1

In 10 ml of a 6 M urea-0.5 M tris-hydroxymethylaminomethane-hydrochloric acid buffer solution of pH 8.0, 2 mg. of insulin (manufactured by Sigma Chemicals Co., Ltd., pig insulin, 25.7 IU/mg) was dissolved (A-solution).

A spectral sensitizer (5 mg.) having formula I:

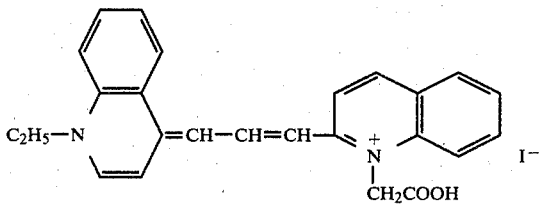

was dissolved in 10 ml. of dimethylformamide. To the resulting solution, 2 µl of isobutyl chloroformate as an activating agent and 1 µl of triethyl amine were added and 1 mg. of N-hydroxysuccinimide was further added to the mixture, under cooling at $-15°$ C. (B-solution).

While stirring the A-solution under ice-cooling, the B-solution was added thereto, followed by reacting for 30 secs. at 4° C. and for further 1 hr. at room temperature. Immediately after completion of the reaction, the labelled insulin thus formed was separated from unreacted material by gel filtration using a Sephadex G-10 column equilibrated with 0.2 M ammonia water (i.e., the pores of the Sephadex G-10 packed in the column were substituted with 0.2 M ammonia water. The separated labelled insulin was then purified using an ion exchange resin (diethylaminoethyl cellulose, weakly acidic) to obtain insulin labelled with the dye, of high purity.

In order to prepare a calibration curve, unlabelled insulin was dissolved in a buffer solution having the same composition as above to obtain standard solutions containing unlabelled insulin in amounts of zero, 5, 10, 20, 40, 80, 160 and 320 µU/ml, respectively. Each of the standard solutions was taken in a small test tube in an amount of 100 µl and a 0.1 M boric acid buffer solution (0.5 ml.) of pH 8.6 was added thereto. Into these respective test tubes, 100 µl of the labelled insulin solution (10 ng/ml) was charged, respectively, and 100 µl of anti-insulin guinea pig blood serum (manufactured by Dynabot Radioisotope Co., Ltd., Tokyo) was further added thereto. After thoroughly stirring the mixture, the system was allowed to stand for 16 hrs. at 4° C.

Thereafter, 100 µl of anti-guinea pig gamma-globulin. diluted blood serum of sheep (second antibody, manufactured by Dynabot Radioisotope Co., Ltd., Tokyo) was added to the system. The mixture was shaken to mix, followed by incubation at 4° C. for 16 hrs. After completion of the incubation, each of the test tubes was subjected to centrifugation at 3000 rpm for 30 mins. Next, the test tubes were carefully taken out and decanted rapidly. Each of the resulting supernatants was moved to a separate test tube.

Each of the thus obtained supernatants (10 µl) was dropwise added onto a 5 mmφ area of a photographic film comprising a support (PET) having coated thereon an unexposed emulsion (AgBrCl, Br content 70 mol%, average grain size 0.7 µm; binder gelatin:PVA=50:50, thickness 4µ, Ag amount 5 g/m², Ag/binder about 1:2 by weight ratio). After allowing the system to stand for 10 mins., the system was exposed to light (10,000 Lux) for 1 sec. through an SC-60 Filter manufactured by Fuji Photo Film Co., Ltd and then developed with Developer A having the composition shown in the following Example 2, at 20° C. for 5 mins.

Following the development, fixing, washing and drying were carried out in succession in a conventional manner. The black density of the photographic film thus processed was measured in a conventional fashion using a densitometer manufactured by Fuji Photo Film Co., Ltd. The results obtained are shown in Table I.

TABLE I

| Concentration of Insulin Standard Solution (µU/ml) | Black Density |
|---|---|
| 0 | 0.20 |
| 5 | 0.51 |
| 10 | 0.85 |
| 20 | 1.15 |
| 40 | 1.35 |
| 80 | 1.85 |
| 160 | 2.20 |
| 320 | 2.53 |

Based on the data obtained above, a calibration curve for use of quantitative analysis of an unknown amount of insulin was obtained and is shown in the figure.

With respect to a solution containing an unknown amount of insulin, the same procedures as above were repeated. From the thus obtained black density data, a concentration of insulin was read using the calibration curve shown in the figure. The amount of insulin was determined to be 10 uU/ml±5. The same procedures were repeated 10 times with one sample. The amount of insulin was always in a range of 10 uU/ml±5, which shows a good reproducibility. The sample tested was blood serum of normal human volunteers with an empty stomach. The determined amount as above was well consistent with the predetermined amount of insulin contained in blood serum taken from a normal human with an empty stomach (see, e.g., NIHON RINSHO (Clinics in Japan), 31, 418 (1973), Shoichi Nakagawa).

While an emulsion (layer) having a specific composition was used in this example, the kind of binder, thickness of an emulsion layer, Ag amount coated, etc. can be varied depending upon necessity; these are well known to one skilled in the art and it is not deemed to require further explanation. However, in general, the amount of silver coated ranges from about 1 to 30 g/m² and the thickness of an emulsion layer from about 1 to about 40 microns.

The black density showed values between 0.51 and 1.04. Ten (10) times repeated procedures provided good reproducibility and accuracy.

The kind of support and the thickness of a support layer can also be easily chosen by one skilled in the art; but, in general, PET, TAC, paper, etc. are typically used at a thickness from about 50 to about 300 microns.

EXAMPLE 2

In a manner similar to Example 1, labelled insulin was obtained except that 5 mg. of insulin and 5 mg. of 3,3'-dicarboxymethyl-meso-bromonaphthothiadicarbocyanine chloride were employed. Yield of the labelled insulin was 100%; even after the purification, the yield was 92%.

As in Example 1, a calibration curve was obtained.

A solution containing an unknown concentration of insulin was added to the purified fraction of the labelled insulin obtained above followed by the same procedures as indicated in Example 1.

Using the supernatant obtained, the black density of the photographic film processed in a manner similar to Example 1 was measured as indicated in Example 1. Developing was performed using Developer A having the following composition.

| Developer A | |
| --- | --- |
| Metol | 0.31 g. |
| Sodium bisulfite | 39.6 g. |
| Hydroquinone | 6.0 g. |
| Sodium carbonate (monohydrate) | 21.9 g. |
| Potassium bromide | 0.86 g. |
| Citric acid | 0.68 g. |
| Potassium metabisulfite | 1.50 g. |
| Water to make 1 liter. | |

EXAMPLE 3

Albumin was labelled with 3,3'-di-(carboxymethyl)-mesoethyl-naphtho[1,2-d]thiacarbocyanine bromide (spectral sensitizer II), whereafter 10 mg. of the thus labelled albumin was taken and dissolved in 100 ml. of deionized water. From the solution (1) a 1.0 ml. sample was taken and put in a test tube (2). Separately, 1.0 ml. of an antialbumin solution in deionized water of an unknown concentration was taken and added to test tube (2). The antigen-antibody reaction product formed by mixing was then separated by gel filtration. The solution (20 μl) obtained by the separation (i.e., unreacted matter in the antigen-antibody reaction) was dropwise added to a 5 mmϕ area on a photographic film comprising a support having coated thereon an unexposed AgBrI emulsion* (I=5 mol%, average grain size 0.7μ). After allowing the system to stand for 10 mins., the system was dried in a conventional manner and exposed to light using an interference filter having a transmission peak around 680 nm. Thereafter, the system was developed with developer B having the following composition at 20° C. for 6 mins.
*binder, gelatin:agar=50:50; Ag amount, 4 g/m²

| Developer B | |
| --- | --- |
| Metol | 2 g. |
| Sodium sulfite (anhydrous) | 40 g. |
| Hydroquinone | 4 g. |
| Sodium carbonate | 28 g. |
| Potassium bromide | 1 g. |
| Water to make 1 liter. | |

*binder, gelatin:agar = 50:50; Ag amount, 4 g/m²

Thereafter, the film was fixed, washed and dried. The resulting density was 0.4. Separately, the same procedure as above was repeated using a solution containing antialbumin of a known concentration to obtain a calibration curve. Based on the calibration curve, the unknown amount of anti-albumin was determined to be 20 mg/l.

EXAMPLE 4

IgG was labelled with spectral sensitizer (III) below.

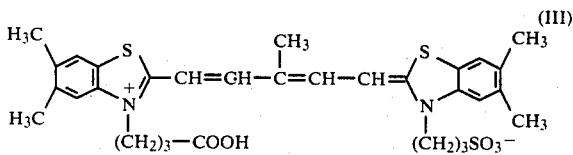

The photographic film used had the same composition as in Example 1 except for: binder, gelatin:acrylamide=50:50, Ag amount 3.5 g/m².

Following the development, fixing and washing were carried out in succession in a conventional manner. The black density of the photographic film thus processed was measured in a conventional fashion using a densitometer manufactured by Fuji Photo Film Co., Ltd.

Separately, a solution containing a known concentration of anti-IgG was prepared as above described and the same procedure as above was performed to obtain a calibration curve. Using the thus obtained calibration curve, the amount of anti-IgG of an unknown concentration in a solution was determined.

However, an AgBrCl emulsion (chlorine 30 mol percent, average grain size 0.65μ) was used instead of an AgBrI emulsion and Developer A was used instead of Developer B. All other conditions were as per Example 3. As a result, precise assay could be made as in Example 3.

The present invention provides advantages that radioactive isotopes are not used but reproducibility and accuracy are comparable with radioimmunoassay; in addition, by properly choosing spectral sensitizers as markers, detection sensitivity can be improved, in other words, silver halides having poor sensitivity can effectively be used.

While the invention has been described in detail and with reference to specific embodiments thereof, it will be apparent to one skilled in the art that various changes and modifications can be made therein without departing from the spirit and scope thereof.

What is claimed is:

1. A method of performing a competitive immunoassay for a trace component in a sample comprising:
   (a) adding a labeled antigen or labeled antibody to said sample in a competitive immunoassay protocol, said label being a spectral sensitizer,
   (b) permitting the immune reactions to take place,
   (c) separating the free labeled antigen or free labeled antibody from the resulting bound labeled antigen or bound labeled antibody,
   (d) contacting either the free labeled immunochemical or the bound labeled immunochemical with silver halide, said immunochemical being either antigen or antibody,
   (e) exposing the resultant of step (d) to light having a wavelength which the spectral sensitizer label absorbs,
   (f) developing the exposed silver halide, and
   (g) measuring the optical density resulting from step (f).

2. The method for competitive immunoassay as claimed in claim 1 wherein the spectral sensitizer has an absorption wavelength region longer than intrinsic absorption wavelength region of silver halide.

3. The method for competitive immunoassay as claimed in claim 2 wherein the absorption wavelength region of said spectral sensitizer is longer than 500 nm.

4. The method for competitive immunoassay as claimed in claim 3 wherein the spectral sensitizer is selected from the group consisting of a cyanine dye, a merocyanine dye, a hemicyanine dye and a styryl dye.

* * * * *